(12) United States Patent
Armer et al.

(10) Patent No.: US 8,044,088 B2
(45) Date of Patent: Oct. 25, 2011

(54) 1-ACETIC ACID-INDOLE DERIVATIVES WITH PGD2 ANTAGONIST ACTIVITY

(75) Inventors: Richard Edward Armer, Cambridge (GB); Edward Andrew Boyd, Henfield (GB); Judith Helen Boyd, legal representative, Henfield (GB); Philip Andrew Hay, Scarborough (GB)

(73) Assignee: Oxagen Limited, Abingdon (GB)

( * ) Notice: Subject to any disclaimer, the term of this patent is extended or adjusted under 35 U.S.C. 154(b) by 825 days.

(21) Appl. No.: 11/908,401

(22) PCT Filed: Mar. 10, 2006

(86) PCT No.: PCT/GB2006/000851
§ 371 (c)(1),
(2), (4) Date: May 13, 2008

(87) PCT Pub. No.: WO2006/095183
PCT Pub. Date: Sep. 14, 2006

(65) Prior Publication Data
US 2010/0330077 A1 Dec. 30, 2010

(30) Foreign Application Priority Data
Mar. 11, 2005 (GB) .................................. 0505048.9

(51) Int. Cl.
*A61K 31/4025* (2006.01)
*A61K 31/404* (2006.01)
*C07D 403/06* (2006.01)

(52) U.S. Cl. ........................................ 514/414; 548/467
(58) Field of Classification Search ......................... None
See application file for complete search history.

(56) References Cited

U.S. PATENT DOCUMENTS

| | | | |
|---|---|---|---|
| 5,641,800 A | 6/1997 | Bach et al. | |
| 6,214,991 B1 | 4/2001 | Jones et al. | |
| 7,534,897 B2 * | 5/2009 | Tanimoto et al. | 548/469 |
| 7,582,672 B2 | 9/2009 | Middlemiss et al. | |
| 7,750,027 B2 | 7/2010 | Armer et al. | |
| 2009/0018138 A1 | 1/2009 | Middlemiss et al. | |
| 2009/0018139 A1 | 1/2009 | Middlemiss et al. | |
| 2009/0018338 A1 | 1/2009 | Middlemiss et al. | |
| 2009/0023788 A1 | 1/2009 | Middlemiss et al. | |
| 2009/0192195 A1 | 7/2009 | Armer et al. | |
| 2010/0022613 A1 | 1/2010 | Armer et al. | |
| 2010/0035956 A1 | 2/2010 | Armer et al. | |
| 2010/0041699 A1 | 2/2010 | Boyd et al. | |
| 2010/0266535 A1 | 10/2010 | Armer et al. | |

FOREIGN PATENT DOCUMENTS

| | | |
|---|---|---|
| EP | 1 505 061 A1 | 2/2005 |
| WO | 03/101981 A1 | 12/2003 |
| WO | 2004/007451 A1 | 1/2004 |
| WO | 2005/019171 A1 | 3/2005 |
| WO | 2005/044260 A1 | 5/2005 |
| WO | 2005/054232 A1 | 6/2005 |
| WO | WO 2009/077728 A1 | 6/2009 |

OTHER PUBLICATIONS

Horig et al. Journal of Translational Medicine, 2:44 (2004).*
Schafer et al. Drug Discovery Today, 13:913 (2008).*
Uller et al. Respiratory Research, 8:16 (2007).*
A.M. Rouhi, Chem. & Eng. News, 81:32 (Feb. 24, 2003).*
Byrn et al. Solid-State Chemistry of Drugs, 2d, Chapter 11 Hydrates and Solvates, 233-247 (1999).*
Morissette et al., Adv. Drug Delivery Rev., 56:275 (2004).*
Grant & Hackh's Chemical Dictionary (5th ed. McGraw-Hill, Inc., 1987).*
Unpublished U.S. Appl. No. 12/779,638, filed May 13, 2010; inventors: Hunter et al., U.S. Patent and Trademark Office, Alexandria, Virginia.
Unpublished U.S. Appl. No. 13/014,314, filed Jan. 26, 2011; inventors: Armer et al., U.S. Patent and Trademark Office, Alexandria, Virginia.
Unpublished U.S. Appl. No. 13/017,860, filed Jan. 31, 2011; inventors: Armer et al., U.S. Patent and Trademark Office, Alexandria, Virginia.

* cited by examiner

*Primary Examiner* — Yong Chu
*Assistant Examiner* — Michael Barker
(74) *Attorney, Agent, or Firm* — Sterne, Kessler, Goldstein & Fox P.L.L.C.

(57) ABSTRACT

Compounds of general formula (I)

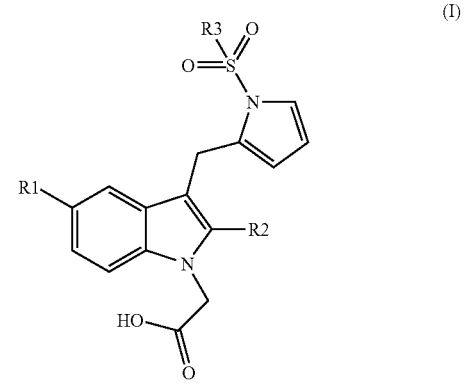

wherein $R^1$ is halo or cyano;
$R^2$ is $C_1$-$C_4$ alkyl; and
$R^3$ is phenyl substituted with one or more substituents chosen from $C_1$-$C_6$ alkyl, halo or —$SO_2(C_1$-$C_6$ alkyl);
or a pharmaceutically acceptable salt, hydrate, solvate, complex or prodrug thereof; are useful in the treatment of diseases and conditions mediated by the action of $PGD_2$ at the CRTH2 receptor.

21 Claims, No Drawings

1-ACETIC ACID-INDOLE DERIVATIVES WITH PGD2 ANTAGONIST ACTIVITY

The present invention relates to compounds which are useful as pharmaceuticals, to methods for preparing these compounds, compositions containing them and their use in the treatment and prevention of allergic diseases such as asthma, allergic rhinitis and atopic dermatitis and other inflammatory diseases mediated by prostaglandin $D_2$ ($PGD_2$) acting at the CRTH2 and/or the DP receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al, (1986), *N. Engl. J. Med.* 315: 800-804). Instillation of $PGD_2$ into airways can provoke many features of the asthmatic response including bronchoconstriction (Hardy et al, (1984) *N. Engl. J. Med.* 311: 209-213; Sampson et al, (1997) *Thorax* 52: 513-518) and eosinophil accumulation (Emery et al, (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al, (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al, (2001) *J. Exp. Med.* 193: 255-261, and EP0851030 and EP-A-1211513 and Bauer et al, EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al, 2001; Monneret et al, (2003) *J. Pharmacol. Exp. Ther.* 304: 349-355). In contrast, the selective DP agonist BW245C does not promote migration of Th2 lymphocytes or eosinophils (Hirai et al, 2001; Gervais et al, (2001) *J. Allergy Clin. Immunol.* 108: 982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune disease, reperfusion injury and a number of inflammatory conditions, all of which are mediated by the action of $PGD_2$ at the CRTH2 receptor.

Compounds which bind to CRTH2 are taught in WO-A-03066046 and WO-A-03066047. These compounds are not new but were first disclosed, along with similar compounds, in GB 1356834, GB 1407658 and GB 1460348, where they were said to have anti-inflammatory, analgesic and antipyretic activity. WO-A-03066046 and WO-A-03066047 teach that the compounds to which they relate are modulators of CRTH2 receptor activity and are therefore of use in the treatment or prevention of obstructive airway diseases such as asthma, chronic obstructive pulmonary disease (COPD) and a number of other diseases including various conditions of bones and joints, skin and eyes, GI tract, central and peripheral nervous system and other tissues as well as allograft rejection.

PL 65781 and JP 43-24418 also relate to indole derivatives which are similar in structure to indomethacin and, like indomethacin, are said to have anti-inflammatory and anti-pyretic activity. Thus, although this may not have been appreciated at the time when these documents were published, the compounds they describe are COX inhibitors, an activity which is quite different from that of the compounds of the present invention. Indeed, COX inhibitors are contraindicated in the treatment of many of the diseases and conditions, for example asthma and inflammatory bowel disease for which the compounds of the present invention are useful, although they may sometimes be used to treat arthritic conditions.

The present inventors have discovered a series of indole acetic acids which are particularly active antagonists of PGD2 at the CRTH2 receptor.

WO-A-9950268, WO-A-0032180, WO-A-0151849 and WO-A-0164205 all relate to indole acetic acids. However, these compounds are said to be aldose reductase inhibitors useful in the treatment of diabetes mellitus (WO-A-9950268, WO-A-0032180 and WO-A-0164205) or hypouricemic agents (WO-A-0151849).

U.S. Pat. No. 4,363,912 also relates to indole acetic acids which are said to be inhibitors of thromboxane synthetase and to be useful in the treatment of conditions such as thrombosis, ischaemic heart disease and stroke. The compounds are all substituted with a pyridyl group.

WO-A-9603376 relates to compounds which are said to be $sPLA_2$ inhibitors which are useful in the treatment of bronchial asthma and allergic rhinitis. These compounds are amides or hydrazides rather than carboxylic acids.

JP 2001247570 relates to a method of producing a 3-benzothiazolylmethyl indole acetic acid, which is said to be an aldose reductase inhibitor.

U.S. Pat. No. 4,859,692 relates to compounds which are said to be leukotriene antagonists useful in the treatment of conditions such as asthma, hay fever and allergic rhinitis as well as certain inflammatory conditions such as bronchitis, atopic and ectopic eczema. However, *J. Med. Chem.*, 6(33), 1781-1790 (1990), which has the same authors as this prior patent application, teaches that compounds with an acetic acid group on the indole nitrogen do not have significant peptidoleukotriene activity. In view of this, it is most surprising that the compounds of the present invention, which all have an acetic acid group on the indole nitrogen, are useful for treating conditions such as asthma, hay fever and allergic rhinitis.

U.S. Pat. No. 4,273,782 is directed imidazole substituted indole acetic acids which are said to be useful in the treatment of conditions such as thrombosis, ischaemic heart disease, stroke, transient ischaemic attack, migraine and the vascular complications of diabetes. There is no mention in the document of conditions mediated by the action of $PGD_2$ at the CRTH2 receptor.

U.S. Pat. No. 3,557,142 relates to 3-substituted-1-indole carboxylic acids and esters which are said to be useful in the treatment of inflammatory conditions.

WO-A-03/097598 relates to compounds which are CRTH2 receptor antagonists. They do not have an aromatic substituent.

Cross et al, *J. Med. Chem.* 29, 342-346 (1986) relates to a process for preparing imidazole-substituted indole acetic acids from the corresponding esters. The compounds to which it relates are said to be inhibitors of thromboxane synthetase.

EP-A-0539117 relates to indole acetic acid derivatives which are said to be leukotriene antagonists.

US 2003/0153751 relates to compounds which are $sPLA_2$ inhibitors. All of the exemplified compounds have bulky substituents at the 2- and 5-positions of the indole system.

US 2004/011648 discloses indole acetic acid derivatives which are inhibitors of PAI-1. There is no suggestion that the compounds might have CRTH2 antagonist activity.

WO 2004/058164 relates to compounds which are said to be asthma and allergic inflammation modulators. There is no demonstration of any activity for indole acetic acid derivatives.

Compounds which bind to the CRTH2 receptor are disclosed in WO-A-03/097042 and WO-A-03/097598. These compounds are indole acetic acids and in WO-A-03/097042 the indole system is fused at the 2-3 positions to a 5-7 membered carbocyclic ring. In WO-A-03/097598 there is a pyrrolidine group at the indole 3-position.

WO-A-03/101981 and WO-A-03/101961 both relate to compound which are said to be CRTH2 antagonists and which are indole acetic acids with an —S— or —$SO_2$— group linked to the indole 3-position.

In our patent application PCT/GB2004/004417, we disclose indole carboxylic acids which are particularly active CRTH2 antagonists. The present application relates to similar compounds which are even more active.

In a first aspect of the present invention, there is provided a compound of general formula (I):

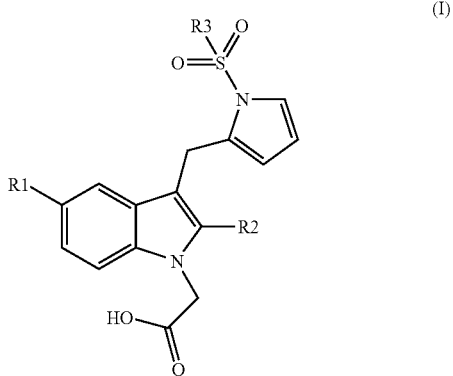

(I)

wherein $R^1$ is halo or cyano;

$R^2$ is $C_1$-$C_4$ alkyl; and $R^3$ is phenyl substituted with one or more substituents chosen from $C_1$-$C_6$ alkyl, halo or —$SO_2$($C_1$-$C_6$ alkyl);

or a pharmaceutically acceptable salt, hydrate, solvate, complex or prodrug thereof.

In the present specification "$C_1$-$C_6$ alkyl" refers to a straight or branched saturated hydrocarbon chain having one to six carbon atoms and optionally substituted with one or more halo substituents or with one or more $C_3$-$C_7$ cycloalkyl groups. Examples include methyl, ethyl, n-propyl, isopropyl, t-butyl, n-hexyl, trifluoromethyl, 2-chloroethyl, methylenecyclopropyl, methylenecyclobutyl and methylenecyclopentyl.

"$C_1$-$C_4$ alkyl" has a similar meaning except that it contains from one to four carbon atoms.

$C_3$-$C_7$ cycloalkyl refers to a saturated 3 to 7 membered carbocyclic ring. Examples of such groups include cyclopropyl, cyclobutyl, cyclopentyl and cyclohexyl.

In the present specification, "halo" refers to fluoro, chloro, bromo or iodo.

Appropriate pharmaceutically and veterinarily acceptable salts of the compounds of general formulae (I) include basic addition salts such as sodium, potassium, calcium, aluminium, zinc, magnesium and other metal salts as well as ammonium, choline, diethylamine, TRIS, diethanolamine, ethanolamine, ethyl diamine, piperazine and other well known basic addition salts.

Where appropriate, pharmaceutically or veterinarily acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts which are not pharmaceutically or veterinarily acceptable may still be valuable as intermediates.

Prodrugs are any covalently bonded compounds which release the active parent drug according to general formula (I) in vivo. Examples of prodrugs include alkyl esters of the compounds of general formula (I), for example the esters of general formula (II) below.

If a chiral centre or another form of isomeric centre is present in a compound of the present invention, all forms of such isomer or isomers, including enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

In preferred compounds of the present invention, independently or in combination, $R^1$ is halo and $R^2$ is methyl or ethyl.

It is particularly preferred that $R^1$ is fluoro and $R^2$ is methyl.

Especially active compounds of the invention include:

[3-(1-Benzenesulfonyl-1H-pyrrol-2-ylmethyl)-5-fluoro-2-methyl-indol-1-yl]-acetic acid;

{5-Fluoro-2-methyl-3-[1-(toluene-4-sulfonyl)-1H-pyrrol-2-ylmethyl]-indol-1-yl}-acetic acid; and {3-[1-(2,4-Difluoro-benzenesulfonyl)-1H-pyrrol-2-ylmethyl]-5-fluoro-2-methyl-indol-1-yl}-acetic acid.

Particularly preferred salts of the compounds of the present invention include:

the potassium, sodium, ammonium, lysine, diethylamine, TRIS, piperazine, ethyl diamine and ethanolamine salts.

The compound of general formula (I) may be derived in vivo from a prodrug. The prodrug may be a compound of general formula (II):

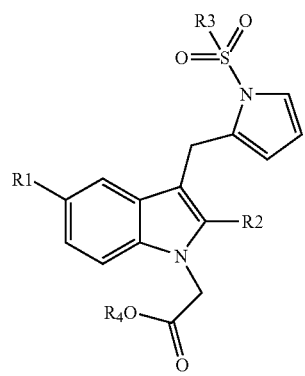

(II)

wherein $R^1$, $R^2$ and $R^3$ are as defined for general formula (I); and $R^4$ is $C_1$-$C_6$ alkyl, aryl, $(CH_2)_m OC(=O)C_1$-$C_6$alkyl, $(CH_2)_m N(R^5)_2$, $CH((CH_2)_m O(C=O)R^6)_2$;

m is 1 or 2;

$R^5$ is hydrogen or methyl;

$R^6$ is $C_1$-$C_{18}$ alkyl.

These compounds of general formula (II) are new and therefore, in a further aspect of the invention there is provided a compound of general formula (II) as defined above or a pharmaceutically acceptable salt, hydrate, solvate, complex or prodrug thereof.

Examples of particularly suitable $R^4$ groups when the compound of general formula (II) is used as a prodrug include:

methyl, ethyl, propyl, phenyl, $CH_2OC(=O)tBu$, $CH_2CH_2N(Me)_2$, $CH_2CH_2NH_2$ or $CH(CH_2O(C=O)R^6)_2$ wherein $R^6$ is as defined above.

Some of the most preferred compounds of general formula (II) are the $C_1$-$C_6$ alkyl, aryl, $(CH_2)_m OC(=O)C_1$-$C_6$alkyl, $(CH_2)_m N(R^5)_2$, $CH((CH_2)_m O(C=O)R^6)_2$ esters of [3-(1-Benzenesulfonyl-1H-pyrrol-2-ylmethyl)-5-fluoro-2-methyl-indol-1-yl]-acetic acid.

When the compound of general formula (II) acts as a prodrug, it is later transformed to the drug by the action of an esterase in the blood or in a tissue of the patient.

Compounds of general formula (I) may be prepared from compounds of general formula (II) in which $R^{12}$ is $C_1$-$C_6$ alkyl by hydrolysis with an alkali such as sodium or lithium hydroxide. The reaction may take place in an aqueous solvent or an organic solvent or a mixture of the two. A typical solvent used for the reaction is a mixture of tetrahydrofuran and water.

Therefore, in a further aspect of the invention, there is provided a process for the preparation of a compound of general formula (I), the process comprising hydrolysing a compound of general formula (II) with a base.

Compounds of general formula (II) may be prepared by reacting a compound of general formula (III):

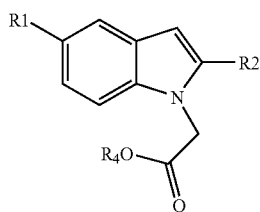

(III)

wherein $R^1$, $R^2$ and $R^4$ are as defined above;
with a compound of general formula (IV):

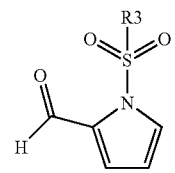

(IV)

wherein $R^3$ is as defined for general formula (I);
under acid conditions.

It is preferred to cool the reaction mixture to a temperature of from about −5 to 5° C. initially and then to complete the reaction at room temperature.

Compounds of general formula (IV) are known to those skilled in the art and are readily available or can be prepared by known methods.

Compounds of general formula (III) can be prepared from compounds of general formula (V):

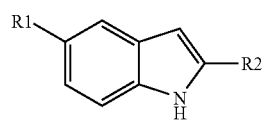

(V)

wherein $R^1$ and $R^2$ are as defined for general formula (I);
by reaction with ethylbromoacetate in the presence of a weak base such as potassium carbonate and in a solvent such as N,N-dimethylformamide (DMF).

Compounds of general formula (V) are readily available or can be prepared by known methods.

The compounds of general formulae (I) and (II) are useful in a method for the treatment of diseases or conditions mediated by the action of $PGD_2$ at the CRTH2 receptor, the method comprising administering to a patient in need of such treatment an appropriate amount of a compound of general formula (I) or (II).

Therefore, in a further aspect of the invention, there is provided a compound of general formula (I) or (II) for use in medicine.

The compounds are particularly useful for the treatment of particularly for use in the treatment or prevention of diseases and conditions mediated by $PGD_2$ at the CRTH2 receptor.

Such diseases and conditions include allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis and also other $PGD_2$-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis and osteoarthritis; and also neurodegenerative diseases such as Alzheimer's disease, Parkinson's disease, stroke and amyotrophic lateral sclerosis.

In a further aspect of the invention, there is provided the use of a compound of general formula (I) or (II) in the preparation of an agent for the treatment of allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, mastocytosis and also other $PGD_2$-mediated diseases, for example autoimmune diseases such as hyper IgE syndrome and systemic lupus erythematus, psoriasis, acne, multiple sclerosis, allograft rejection, reperfusion injury, chronic obstructive pulmonary disease, as well as rheumatoid arthritis, psoriatic arthritis and osteoarthritis and neurodegenerative diseases such as Alzheimer's disease, Parkinson's disease, stroke and amyoptrophic lateral sclerosis.

The compounds of general formula (I) or (II) must be formulated in an appropriate manner depending upon the diseases or conditions they are required to treat.

Therefore, in a further aspect of the invention there is provided a pharmaceutical composition comprising a compound of general formula (I) or (II) together with a pharmaceutical excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for non-oral delivery, for example, nasal, buccal or topical administration, including topical administration to the eye, intravenous, bronchial, intramuscular, subcutaneous administration.

Such compositions are particularly useful in the treatment of diseases and conditions such as allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, ulcerative colitis, autoimmune diseases such as psoriasis, acne, multiple sclerosis, chronic obstructive pulmonary disease, as well as rheumatoid arthritis, psoriatic arthritis and osteoarthritis.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a novel compound of general formula (I) or (II) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

As mentioned above, however, it is preferred that the compound is administered by a route other than the oral route. For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (II) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit $PGD_2$ at the CRTH2 receptor. The precise amount of a compound of general formula (I) or (II) which is therapeutically effective, and the route by which such compound is best administered, is readily determined by one of ordinary skill in the art by comparing the blood level of the agent to the concentration required to have a therapeutic effect.

Compounds of general formula (I) or (II) may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of a compound of general formula (I) or (II) in the preparation of an agent for the treatment of diseases and conditions mediated by $PGD_2$ at the CRTH2 receptor, wherein the agent also comprises an additional active agent useful for the treatment of the same diseases and conditions.

These additional active agents which may have a completely different mode of action include existing therapies for allergic and other inflammatory diseases including:

β2 agonists such as salmeterol;

corticosteroids such as fluticasone;

antihistamines such as loratidine;

leukotriene antagonists such as montelukast;

anti-IgE antibody therapies such as omalizumab;

anti-infectives such as fusidic acid (particularly for the treatment of atopic dermatitis);

anti-fungals such as clotrimazole (particularly for the treatment of atopic dermatitis);

immunosuppressants such as tacrolimus and particularly pimecrolimus in the case of inflammatory skin disease.

CRTH2 antagonists may also be combined with therapies that are in development for inflammatory indications including:

other antagonists of $PGD_2$ acting at other receptors, such as DP antagonists;

inhibitors of phoshodiesterase type 4 such as cilonilast;

drugs that modulate cytokine production such as inhibitors of TNFα converting enzyme (TACE);

drugs that modulate the activity of Th2 cytokines IL-4 and IL-5 such as blocking monoclonal antibodies and soluble receptors;

PPAR-γ agonists such as rosiglitazone;

5-lipoxygenase inhibitors such as zileuton.

In yet a further aspect of the invention, there is provided a product comprising a compound of general formula (I) or (II) and one or more of the agents listed above as a combined preparation for simultaneous, separate or sequential use in the treatment of a disease or condition mediated by the action of $PGD_2$ at the CRTH2 receptor.

The invention will now be described in greater detail with reference to the following non limiting example.

EXAMPLE 1

Preparation of [3-(1-Benzenesulfonyl-1H-pyrrol-2-ylmethyl)-5-fluoro-2-methyl-indol-1-yl]-acetic acid (Compound 1)

a. Ethyl-(5-fluoro-2-methylindolyl-1-acetate)

Potassium carbonate (139.1 g, 1.0 mol) was added in one portion to a stirred solution of 5-fluoro-2-methylindole (30.0 g, 0.2 mol) in N,N-dimethylformamide (300 ml) at room temperature. Ethyl bromoacetate (22.3 ml, 0.2 mol) was then added in one portion and the resulting mixture stirred at 90° C. for 18 h. An excess of potassium carbonate (69.1 g, 0.5 mol) and ethyl bromoacetate (11.1 ml, 0.1 mol) were then added and the mixture stirred at 90° C. for a further 24 h. Potassium carbonate (27.6 g, 0.2 mol) was then added and the mixture stirred at 90° C. for 24 h, cooled to room temperature and then water (500 ml) was added. The product was extracted with ethyl acetate (5×500 ml) and combined organic extracts were then dried and concentrated in vacuo to leave a viscous brown oil which was purified by flash column chromatography on silica gel eluting with ethyl acetate:heptane (2:1) to give the ester (22.84 g, 48%) as a beige solid, $\delta_H$ (250 MHz, CDCl$_3$) 7.18 (1H, dd J 9.5, 2.4 Hz, Ar), 7.08 (1H, dd, J 8.8, 4.2 Hz, Ar), 6.89 (1H, td, J 9.1, 2.5 Hz, Ar), 6.27 (1H, s, CH), 4.76 (2H, s, CH$_2$CO$_2$Et), 4.22 (2H, q, J 7.1 Hz, CH$_2$COCH$_2$CH$_3$), 2.4 (3H, s, CCH$_3$), 1.26 (3H, t, J 7.1 Hz, CH$_2$COCH$_2$CH$_3$); Tr=1.51 min, m/z (ES$^+$), (M+H)$^+$ 236.20.

b. [3-(1-Benzenesulfonyl-1H-pyrrol-2-ylmethyl)-5-fluoro-2-methyl-indol-1-yl]-acetic acid ethyl ester Triethylsilane (1.3 ml, 8 mmol) and trifluoroacetic acid (0.36 ml, 5 mmol) were sequentially added dropwise to a stirred solution of (5-fluoro-2-methyl-indol-1-yl)-acetic acid ethyl ester (379 mg, 1.61 mmol) and phenylsulfonyl pyrrole-2-carboxaldehyde (411 mg, 1.75 mmol) in dichloromethane (20 ml) at 0° C. The mixture was stirred at 0° C. for 1 h and then at room temperature for 3 h. The resulting mixture was diluted with dichloromethane (50 ml), washed with a saturated solution of sodium bicarbonate (2×50 ml), brine (50 ml), dried and then concentrated in vacuo. Trituration with tert-butyl methyl ether and heptane gave the indole (458 mg, 62%) as a light brown solid, Tr=1.74 min (96%), m/z (ES$^+$) (M+H)$^+$ 455.01.

c. [3-(1-Benzenesulfonyl-1H-pyrrol-2-ylmethyl)-5-fluoro-2-methyl-indol-1-yl]-acetic acid Lithium hydroxide monohydrate (138 mg, 3.3 mmol) was added in one portion to a stirred solution of [3-(1-benzenesulfonyl-1H-pyrrol-2-ylmethyl)-5-fluoro-2-methyl-indol-1-yl]-acetic acid ethyl ester (507 mg, 1.1 mmol) in tetrahydrofuran:water (2:1; 10 ml) and the resulting mixture stirred at room temperature for 3 h. The solution was adjusted to pH 1 with 1M hydrochloric acid and then concentrated in vacuo to leave a yellow solid. The solid was partitioned between ethyl acetate (30 ml) and water (30 ml) and then the organic layer separated. The aqueous layer was extracted with ethyl acetate (2×20 ml) and the combined organic extracts were then dried and concentrated in vacuo to leave an off-white solid. Purification by flash column chromatography on silica gel eluting with 10% methanol:dichloromethane gave the carboxylic acid (130 mg, 28%) as a white solid, $\delta_H$ (250 MHz, d$_6$-DMSO) 7.84 (2H, d J 7.1 Hz, Ar), 7.74 (1H, d J 7.1 Hz, Ar), 7.65-7.59 (2H, m, Ar), 7.44-7.41 (1H, m, Ar), 7.35-7.30 (1H, m, Ar), 6.82 (1H, td J 9.3, 2.4 Hz, Ar), 6.42 (1H, dd J 9.8, 2.4 Hz, Pyrrole-CH), 6.23-6.21 (1H, m, Pyrrole-CH), 5.56 (1H, br s, Pyrrole-CH), 4.94 (2H, s, CH$_2$-Pyrrole), 4.02 (2H, s, CH$_2$CO$_2$H), 2.52 (3H, masked s, CCH$_3$); Tr=1.63, m/z (ES$^+$) (M+H)$^+$ 427.19.

EXAMPLE 2

Synthesis of {5-Fluoro-2-methyl-3-[1-(toluene-4-sulfonyl)-1H-pyrrol-2-ylmethyl]-indol-1-yl}-acetic acid (Compound 2)

Compound 2 was prepared according to the procedure described for Compound 1 using appropriately chosen starting materials. $\delta_H$ (400 MHz, d$_6$-DMSO) 7.68 (2H, d J 8.6 Hz, Ar), 7.38 (3H, m, Ar), 7.29 (1H, dd J 8.8, 4.4 Hz, Ar), 6.79 (1H, td J 9.2, 2.5 Hz, Ar), 6.27 (1H, dd J 10.0, 2.4 Hz, Ar), 6.19 (1H, t J 3.4 Hz, Pyrrole-CH), 5.55 (1H, m, Pyrrole-CH), 4.92 (2H, s, CH$_2$-Pyrrole), 3.98 (2H, s, CH$_2$CO$_2$H), 2.37 (3H, s, CCH$_3$), 2.10 (3H, s, ArCH$_3$); Tr=2.11, m/z (ES$^+$) (M+H)$^+$ 441.26.

EXAMPLE 3

Synthesis of {3-[1-(2,4-Difluoro-benzenesulfonyl)-1H-pyrrol-2-ylmethyl]-5-fluoro-2-methyl-indol-1-yl}-acetic acid Compound 3 was prepared according to the procedure described for Compound 1 using appropriately chosen starting materials. $\delta_H$ (400 MHz, d$_6$-DMSO) 7.69 (1H, m, Ar), 7.42 (1H, m, Ar), 7.34 (1H, m, Ar), 7.23 (1H, dd J 8.8, 4.4 Hz, Ar), 7.09 (1H, td J 8.2, 2.3 Hz, Ar), 6.76 (1H, td J 9.3, 2.4 Hz, Ar), 6.35 (1H, dd J 10.2, 2.4 Hz, Ar), 6.26 (1H, t J 3.4 Hz, Ar), 5.86 (1H, bs, Pyrrole-CH), 4.88 (2H, s, CH$_2$-Pyrrole), 4.01 (2H, s, CH$_2$CO$_2$H), 2.15 (3H, s, CCH$_3$); Tr=2.17, m/z (ES$^+$) (M+H)$^+$ 463.09.

EXAMPLE 4

Measurement of CRTH2 Antagonist Activity

Materials and Methods
Materials
Calcium-3 dye was purchased from Molecular Devices (Wokingham, UK). Mono-.poly resolving medium was obtained from Dainippon Pharmaceuticals (Osaka, Japan). Macs anti-CD16 microbeads were from Miltenyi biotec (Bisley, Surrey). ChemoTx plates were purchased from Neuroprobe (Gaithesburg, Md.). Poly-D-lysine coated 96-well plates were obtained from Greiner (Gloucestershire, UK). [$^3$H]PGD$_2$ was from Amersham Biosciences (Buckinghamshire, UK). [$^3$H]SQ29548 was purchased from Perkin Elmer Life Sciences (Buckinghamshire, UK). All other reagents were obtained from Sigma-Aldrich (Dorset, UK), unless otherwise stated.
Methods
Cell Culture
Chinese Hamster Ovary cells were transfected with CRTH2 or DP receptors (CHO/CRTH2 and CHO/DP) and were maintained in culture in a humidified atmosphere at 37° C. (5% CO$_2$) in Minimum Essential Medium (MEM) supplemented with 10% foetal bovine serum, 2 mM glutamine, and 1 mg ml$^{-1}$ active G418. The cells were passaged every 2-3 days. For radioligand binding assay, cells were prepared in triple-layer flasks or in 175 cm$^2$ square flasks (for membrane preparation). For calcium mobilisation assay, cells were grown in a 96 well plate 24h prior to the assay at a density of 80,000 cells per well.

Preparation of Cell Membranes

Membranes were prepared either from CHO/CRTH2 and CHO/DP cells, or from platelets (as a source of TP receptors). CHO cells grown to confluency were washed with PBS and detached using a Versene solution (15 ml per flask). When the cells were grown in 175 cm$^2$ square flask, they were collected by scrapping in PBS. The cell suspensions were centrifuged (1,700 rpm, 10 min, 4° C.) and resuspended in 15 ml of buffer (1×HBSS, supplemented with 10 mM HEPES, pH 7.3). Cell suspensions were then homogenised using an Ultra Turrax at setting 4-6 for 20 s. The homogenate was centrifuged at 1,700 rpm for 10 min and the supernatant was collected and centrifuged at 20,000 rpm for 1 h at 4° C. The resulting pellet was resuspended in buffer and stored at −80° C. in aliquots of 200-500 µl. The protein concentration was determined by the method of Bradford (1976), using bovine serum albumin as standard. The platelets were washed by centrifugation at 600×g for 10 min and resuspended in ice-cold assay buffer (10 mM Tris-HCl, pH 7.4, 5 mM Glucose, 120 mM NaCl, 10 µM indomethacin) and directly centrifuged at 20,000 rpm for 30 min at 4° C. The resulting pellet was treated as described above.

Radioligand Binding Assays

[$^3$H]PGD$_2$ (160 Ci/mmol) binding experiments were performed on membranes prepared as described above. Assays were performed in a final volume of 100 µl of buffer (1×HBSS/HEPES 10 mM, pH 7.3). Cell membranes (15 µg). Cell membranes 15 mg were preincubated at room temperature with varying concentration of competing ligand for 15 min. [$^3$H]PGD$_2$ (mol, final concentration) was then added and the incubation continued for a further one hour at room temperature. The reaction was terminated by the addition of 200 µl ice-cold assay buffer to each well, followed by rapid filtration through Whatman GF/B glass fibre filters using a Unifilter Cell harvester (PerkinElmer Life Sciences) and six washes of 300 µl of ice-cold buffer. The Unifilter plates were dried at room temperature for at least 1 h and the radioactivity retained on the filters was determined on a Beta Trilux counter (PerkinElmer Life Sciences), following addition of 40 µl of Optiphase Hi-Safe 3 (Wallac) liquid scintillation. Non specific binding was defined in the presence of 10 µM unlabelled PGD$_2$. Assays were performed in duplicate.

The results of the radioligand binding experiments for the binding of Compounds 1 and 2 to the CRTH2 and DP receptors are shown in Table 1.

TABLE 1

| Compound | Binding to CRTH2 Receptor Ki (nM) | Binding to DP Receptor Ki (nM) |
| --- | --- | --- |
| 1 | 1 | 9202 |
| 2 | 0.2 | 1800 |
| 3 | 2 | 8000 |

The invention claimed is:

1. A compound of general formula (II):

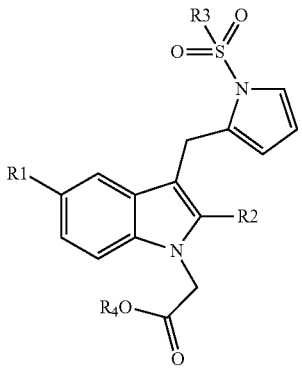

wherein $R^1$ is halo or cyano; $R^2$ is $C_1$-$C_4$ alkyl;
$R^3$ is phenyl substituted with one or more substituents chosen from $C_1$-$C_6$ alkyl, halo or —$SO_2$($C_1$-$C_6$ alkyl);
$R^4$ is hydrogen, $C_1$-$C_6$ alkyl, aryl, $(CH_2)_mOC(=O)C_1$-$C_6$alkyl, $(CH_2)_mN(R^5)_2$, or $CH((CH_2)_mO(C=O)R^6)_2$;
m is 1 or 2;
$R^5$ is hydrogen or methyl; and
$R^6$ is $C_1$-$C_{18}$ alkyl;
or a pharmaceutically acceptable salt thereof.

2. A compound of claim 1 having the general formula (I):

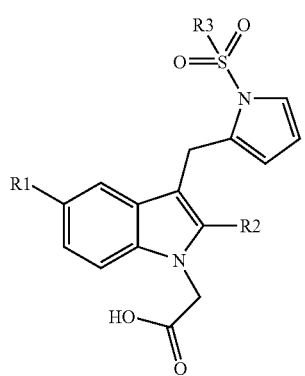

wherein $R^1$ is halo or cyano;
$R^2$ is $C_1$-$C_4$ alkyl; and
$R^3$ is phenyl substituted with one or more substituents chosen from $C_1$-$C_6$ alkyl, halo or —$SO_2$($C_1$-$C_6$ alkyl);
or a pharmaceutically acceptable salt thereof.

3. A salt of a compound as claimed in claim 1, which is the sodium, potassium, calcium, aluminium, zinc, magnesium, ammonium, choline, diethylamine, TRIS, diethanolamine, ethanolamine, ethyl diamine, piperazine, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate or succinate salt, or an organic sulfonic acid salt selected from the group consisting of methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; or an inorganic acid salt selected from the group consisting of hydrochloride, hydrobromide, hydroiodide, sulfate, bisulfate, hemisulfate, thiocyanate, persulfate, phosphoric acid and sulfonic acid salt.

4. A compound as claimed claim 1, wherein, independently or in combination, $R^1$ is halo and $R^2$ is methyl or ethyl.

5. A compound as claimed in claim 4, wherein $R^1$ is fluoro and $R^2$ is methyl.

6. [3-(1-Benzenesulfonyl-1H-pyrrol-2-ylmethyl)-5-fluoro-2-methyl-indol-1-yl]-acetic acid;
{5-Fluoro-2-methyl-3-[1-(toluene-4-sulfonyl)-1H-pyrrol-2-ylmethyl]-indol-1-yl}-acetic acid; or
{3-[1-(2,4-Difluoro-benzenesulfonyl)-1H-pyrrol-2-ylmethyl]-5-fluoro-2-methylindol-1-yl}-acetic acid;
or the $C_1$-$C_6$ alkyl, aryl, $(CH_2)_mOC(=O)C_1$-$C_6$alkyl, $(CH_2)_mN(R^5)_2$ or $CH((CH_2)_mO(C=O)R^6)_2$ ester thereof, wherein $R^5$ is hydrogen or methyl and $R^6$ is $C_1$-$C_{18}$ alkyl, or a pharmaceutically acceptable salt thereof.

7. A process for the preparation of a compound, having the general formula (I):

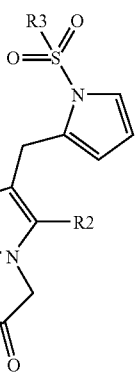

the process comprising hydrolysing a compound as claimed in claim 1 with a base.

8. A method for treating a subject suffering from or at risk for acquiring a $PGD_2$-mediated disease comprising administering to the subject a compound of claim 1 in an amount effective to inhibit $PGD_2$ wherein the $PGD_2$-mediated disease is selected from the group consisting of allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis and Crohn's disease, mastocytosis, and autoimmune diseases.

9. A pharmaceutical composition comprising a compound as claimed in claim 1 together with a pharmaceutical excipient or carrier.

10. A pharmaceutical composition as claimed in claim 9 for administration by the nasal, buccal or topical administration, including topical administration to the eye.

11. A pharmaceutical composition as claimed in claim 9 further including an additional active agent.

12. The method of claim 8 which further comprises administering to the subject an additional active agent.

13. A pharmaceutical composition as claimed in claim 11 wherein the additional active agent comprises:
β2 agonists;
corticosteroids;
antihistamines;

leukotriene antagonists;
anti-IgE antibody therapies;
anti-infectives;
anti-fungals;
immunosuppressants;
antagonists of $PGD_2$ acting at other receptors;
inhibitors of phosphodiesterase type 4;
drugs that modulate cytokine production;
drugs that modulate the activity of Th2 cytokines IL-4 and BL-5;
PPAR-γ agonists; or
5-lipoxygenase inhibitors.

14. A method for treating a subject suffering from or at risk for acquiring allergic asthma, perennial allergic rhinitis, seasonal allergic rhinitis, atopic dermatitis, contact hypersensitivity, conjunctivitis, allergic conjunctivitis, eosinophilic bronchitis, food allergies, eosinophilic gastroenteritis, inflammatory bowel disease, ulcerative colitis, Crohn's disease, mastocytosis, or autoimmune diseases comprising administering to the subject an amount effective to inhibit $PGD_2$ in the subject of a compound of claim 1 and simultaneously, separately or sequentially administering to the subject one or more additional active agents useful for the treatment of diseases and conditions mediated by $PGD_2$ at the CRTH2 and/or DP receptor.

15. The method of claim 8, wherein the PGD2-mediated disease is an autoimmune disease selected from the group consisting of hyper IgE syndrome, systemic lupus erythematus, psoriasis, acne, multiple sclerosis, allograft rejection, reperfusion injury, chronic obstructive pulmonary disease, rheumatoid arthritis, psoriatic arthritis and osteoarthritis.

16. A pharmaceutical composition as claimed in claim 13, wherein the additional active agents are selected from the group consisting of salmeterol, fluticasone, loratidine, montelukast, omalizumab, fusidic acid, clotrimazole, tacrolimus, pimecrolimus, DP antagonists, cilonilast, inhibitors of TNFα converting enzyme (TACE), monoclonal antibodies, soluble receptors that modulate the activity of Th2 cytokines IL-4 and IL-5, rosiglitazone and zileuton.

17. The compound according to claim 6 which is [3-(1-Benzenesulfonyl-1H-pyrrol-2-ylmethyl)-5-fluoro-2-methyl-indol-1-yl]-acetic acid, or a pharmaceutically acceptable salt thereof.

18. The compound according to claim 6 which is {5-Fluoro-2-methyl-3-[1-(toluene-4-sulfonyl)-1H-pyrrol-2-ylmethyl]-indol-1-yl}-acetic acid, or a pharmaceutically acceptable salt thereof.

19. The compound according to claim 6 which is {3-[1-(2,4-Difluoro-benzenesulfonyl)-1H-pyrrol-2-ylmethyl]-5-fluoro-2-methylindol-1-yl}-acetic acid, or a pharmaceutically acceptable salt thereof.

20. A pharmaceutical composition as claimed in claim 13 wherein the additional active agent is a leukotriene antagonist.

21. A pharmaceutical composition as claimed in claim 20 wherein the leukotriene antagonist is montelukast.

* * * * *